United States Patent
Ueno et al.

(10) Patent No.: US 7,432,502 B2
(45) Date of Patent: Oct. 7, 2008

(54) INFORMATION ACQUISITION METHOD AND APPARATUS FOR INFORMATION ACQUISITION

(75) Inventors: Rie Ueno, Hadano (JP); Ikuo Nakazawa, Zama (JP)

(73) Assignee: Canon Kabushiki Kaisha, Tokyo (JP)

( * ) Notice: Subject to any disclaimer, the term of this patent is extended or adjusted under 35 U.S.C. 154(b) by 441 days.

(21) Appl. No.: 10/543,492

(22) PCT Filed: Mar. 3, 2004

(86) PCT No.: PCT/JP2004/002687

§ 371 (c)(1),
(2), (4) Date: Jul. 27, 2005

(87) PCT Pub. No.: WO2004/079344

PCT Pub. Date: Sep. 16, 2004

(65) Prior Publication Data

US 2006/0169918 A1   Aug. 3, 2006

(30) Foreign Application Priority Data

Mar. 6, 2003 (JP) .............................. 2003-060436
Feb. 24, 2004 (JP) .............................. 2004-047814

(51) Int. Cl.
*H01J 40/00* (2006.01)

(52) U.S. Cl. ............ 250/307; 250/305; 250/311; 250/306

(58) Field of Classification Search ...... 250/306–443.1, 250/305

See application file for complete search history.

(56) References Cited

U.S. PATENT DOCUMENTS

| 4,590,792 A | * | 5/1986 | Chiang ............... 73/28.06 |
| 4,888,956 A | | 12/1989 | le Roux Murray ...... 62/51.1 |
| 5,230,219 A | * | 7/1993 | Ichikawa et al. ......... 62/78 |
| 5,753,924 A | * | 5/1998 | Swann ............... 250/443.1 |

FOREIGN PATENT DOCUMENTS

| EP | 0 275 114 A2 | 7/1988 |
| GB | 1 230 120 | 4/1971 |
| JP | 9-57091 | 3/1997 |

* cited by examiner

*Primary Examiner*—Jack I. Berman
*Assistant Examiner*—Andrew Smyth
(74) *Attorney, Agent, or Firm*—Fitzpatrick, Cella, Harper & Scinto

(57) ABSTRACT

The invention is to provide a method and an apparatus for observing a substance having a stable morphology in a liquid medium such as water. The method comprises the steps of obtaining a composition in which the substance is maintained in a liquid medium, bringing the liquid medium into an amorphous state, and acquiring information relating to the substance by observing the substance in the amorphous medium using an electron microscope

5 Claims, 5 Drawing Sheets

INFORMATION ACQUISITION METHOD AND APPARATUS FOR INFORMATION ACQUISITION

TECHNICAL FIELD

The present invention relates to a method for acquiring information relating to the morphology of a material in a liquid medium.

BACKGROUND ART

With recent development of functional materials, there are provided, for example, materials such as microcapsules of which shape can be maintained only in a liquid medium. For example, it has been proposed an ink for ink jet recording containing a microencapsulated functional substance to improve color developing properties and weather resistance. In such a case, it is very important to do analysis and evaluation of the microcapsules on shape, composition etc. thereof to know the ink properties.

One of the conventional evaluation methods is scanning electron microscopy. Japanese Patent Application Laid-open No. H09-057091 discloses a method for observing a cross section of microcapsules including a volatile substance by using an ordinary scanning electron microscope.

In case of microcapsules dispersed in water, the above method first separates the microcapsules from water and observes the inside of the microcapsules having a resinous shell. Thus, the real shape of the microcapsules in a liquid medium in actual use may not be obtained by such a method.

In general, a sample of high molecular substance holding its shape in a liquid medium such as water, for example, a water-containing sol or gel, loses its structure when placed in a scanning electron microscope due to water evaporation. In addition, such a sample has a high electrical resistance without electrical conductivity, so that it is charged up and a secondary electron image cannot be obtained.

Therefore, such a sample is observed and analyzed most suitably by using an environment-controlled scanning electron microscope.

Such environment-controlled scanning electron microscope is also called a low vacuum scanning electron microscope, where the observation is carried out under a low (poor) vacuum level in comparison with the ordinary scanning electron microscope.

In such a low vacuum scanning electron microscope, however, a residual gas remaining in the chamber due to the low vacuum level hinders flight of the secondary electrons generated from the sample to a detector, whereby a detected signal level becomes low and a sufficient resolution cannot be obtained.

DISCLOSURE OF THE INVENTION

In consideration of the foregoing, the present invention provides an information acquiring method and an apparatus for information acquisition on the morphology in a liquid medium, for example, the morphology of microcapsules or the like in a liquid medium such as water.

In order to attain the aforementioned object, the present invention provides an information acquiring method for acquiring morphological information on a substance in a liquid medium that comprises the following steps:

(a) maintaining a substance in a liquid medium;
(b) bringing the liquid medium into an amorphous state; and
(c) subjecting the substance maintained in the amorphous medium to an electron microscopic observation to acquire information relating to the substance.

More specifically, the present invention is characterized in that a sample containing a liquid medium such as water is frozen by a rapid freezing method, transferred to a cryogenic transmission electron microscope by a cryogenic transfer method and observed in a frozen state.

It is also characterized in that, in such observation, an energy filtering transmission electron microscope is used for improved contrast.

BEST MODE FOR CARRYING OUT THE INVENTION

Figure 1:
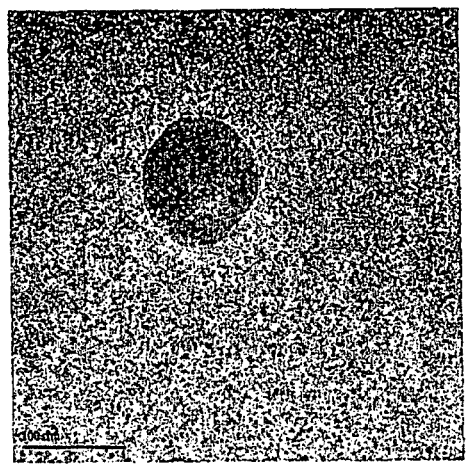
FIG. 1 is a transmission electron photomicrograph (magnification: ×40,000) showing a particle structure of an ink, obtained in an evaluation of Example 1.
Figure 2:
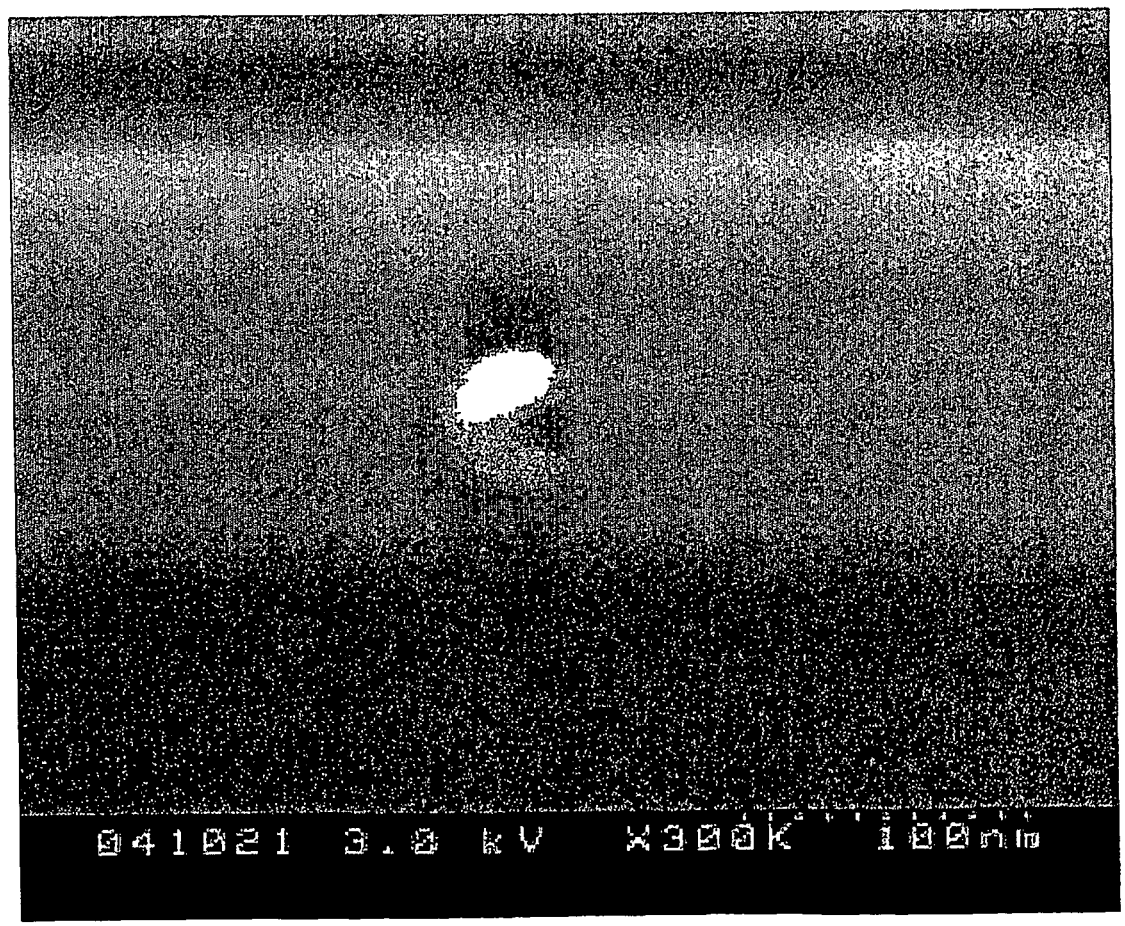
FIG. 2 is a transmission electron photomicrograph (magnification: ×300,000) showing a particle structure of microcapsules, obtained in an evaluation of Example 2.
Figure 3:
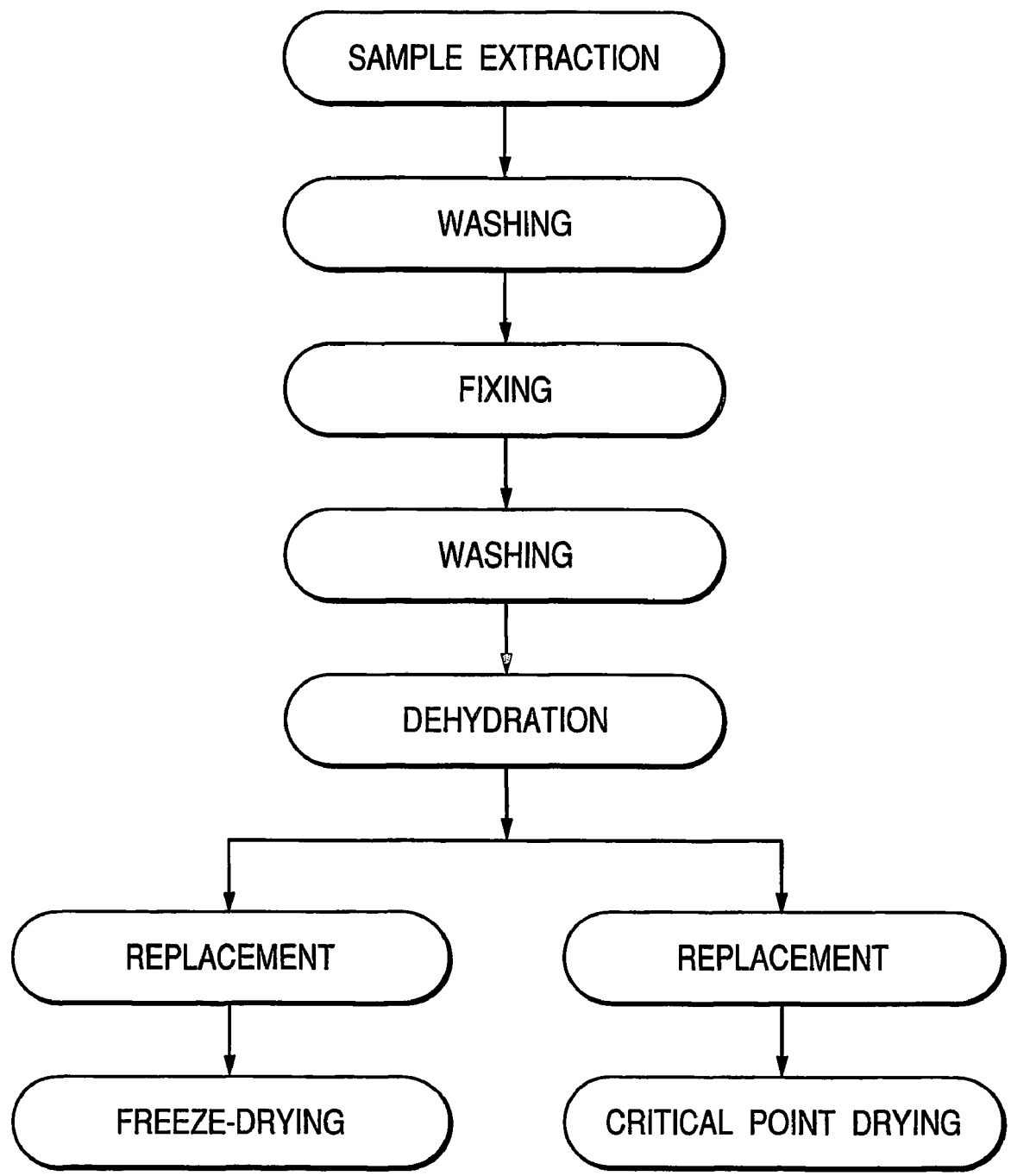
FIG. 3 is a flow chart showing a process of a prior evaluation process.
Figure 4:
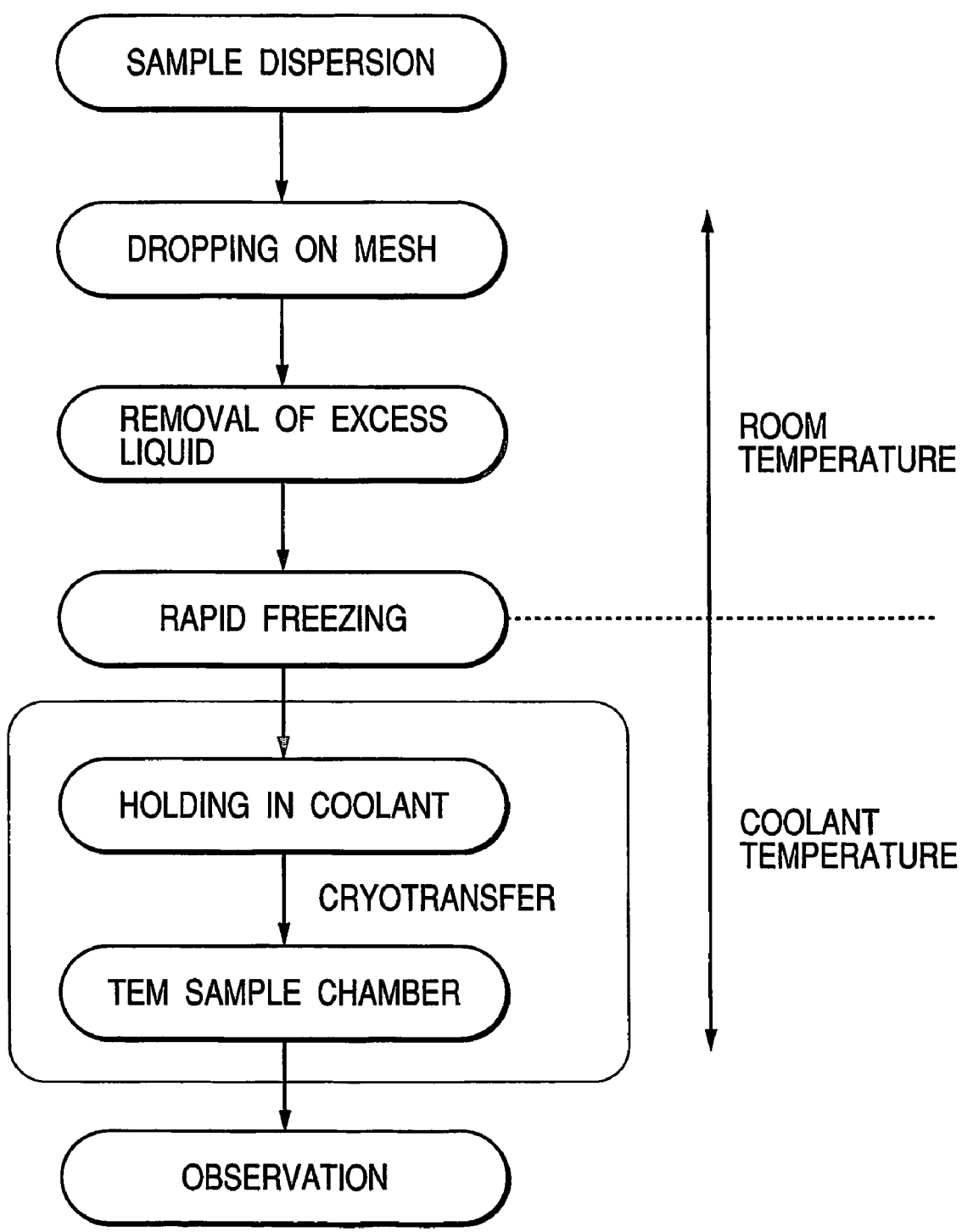
FIG. 4 is a flow chart showing an evaluation process of the present invention.

The present invention provides a method for acquiring information on morphology of a substance in a liquid medium, of which shape in a liquid medium is different from that outside the liquid medium.

When this method is applied to a microencapsulated substance, it enables evaluation of the microcapsules analyzing the morphology of the microcapsules and qualitative and quantitative analysis of the encapsulated substance during the production process of a composition comprised of a liquid medium and the microcapsules.

The aforementioned substance can be various functional substances, for example a coloring material such as a pigment or a dye employed in an ink or a toner, a color developing substance such as α-naphthol or the like, and a catalytic substance such as alumina or silica. It can also be a microorganism such as fungi (mold) and botulinus bacterium, but not limited thereto.

Also microencapsulation of such a substance means that the substance is apparently covered, and the substance may partly protrude from the capsule. Also the capsule need not necessarily be in a form of a shell or a film but may contain more liquid medium in an outer part to swell.

Also the aforementioned liquid medium can be water, a water-soluble liquid medium or organic solvent such as ethanol, methanol and toluene. The liquid medium is preferably brought to an amorphous state prior to the analysis. This means that the liquid medium preferably becomes a substantially amorphous solid. Of course, this state may include a crystalline material or an amorphous gel.

The liquid medium can be brought into an amorphous state by rapid freezing or rapid freeze fixation. In the field of biology, various freezing methods are attracting attention for sample preparation to analyze fine structures of cells or tissues containing water and lipid. These methods instantaneously freeze the cells or tissues containing a large amount of water in the living state confining the components of cells or tissues and various substances in the ice, to provide a specimen that allows morphological analysis or in situ detection of substances, based on a concept of "carrying out analysis maintaining the living state". However, the largest drawback of such freezing methods is that when water turns ice, ice crystals gradually grow to distort the structure of the sample. In particular, a sufficient resolution cannot be obtained in high resolution analysis or observation.

With improvement of the freezing apparatus, the rapid freeze fixation method can suppress the structural disruption due to the ice crystal formation (water molecules in a liquid phase assemble in a certain regular orientation around a core material (a crystal core), thereby providing a specimen suitable for morphological analysis.

Therefore, in the freezing method, it is important to make the cooling speed as fast as possible. For this purpose, it is preferable to employ a coolant of which melting point is as low as possible, and to increase the heat conductivity between the sample and the coolant.

The above method to be used for electron microscopic observation of a sample containing water and lipid may be called "cryotransfer", that is, the sample is rapidly frozen and fixed to maintain the original state and introduced under the same environment (temperature and humidity) into the electron microscope.

For morphological analysis of microcapsules and qualitative and quantitative analysis of the included substance, it is preferable to employ the energy filtering electron microscope. The energy filtering electron microscope is a transmission electron microscope (TEM) equipped with an energy filter (EF). By incorporating the energy filter into a transmission electron microscope, electron beams passed through the sample can be subjected to spectroscopy, thereby obtaining three-dimensional information comprised of two dimensional information on image and information of electron energy loss spectrometry (EELS) of inelastic scattering electrons at a spatial resolution of the TEM. An EF image can be obtained by forming a TEM image selecting only electrons that lost a specified energy by means of EFTEM-EELS, whereby it becomes possible to observe an organic substance with a high contrast, which has been difficult. It is also possible to carry out composition analysis, point analysis, linear analysis or mapping of a specimen.

EXAMPLES

In the following, the present invention is further explained with examples, but the present invention is not limited to such examples.

Example 1

Synthesis of Block Polymer

A block polymer having a carboxylic acid at an end, constituted of monomer units of 2-ethoxyethyl vinyl ether (EOVE), 2-methoxyethyl vinyl ether (MOVE) and $HO(CH_2)_5 COOH$ was synthesized Poly[EOVE (2-ethoxyethyl vinyl ether)-b-MOVE (methoxyethyl vinyl ether)]-$O(CH_2)_5COOH$ (wherein b is a symbol indicating a block polymer) was synthesized by a following process.

A glass container equipped with a three-way stopcock was prepared, purged with nitrogen, and then heated at 250° C. under a nitrogen atmosphere to eliminate adsorbed water. After the system was cooled to the room temperature, 12 mmol (millimoles) of EOVE, 16 mmol of ethyl acetate, 0.1 mmol of 1-isobutoxyethyl acetate and 11 ml of toluene were added and the reaction system was cooled. When the temperature in the system reached 0° C., 0.2 mmol of ethyl aluminum sesquichloride (an equimolar mixture of diethyl aluminum chloride and ethyl aluminum dichloride) were added to initiate a polymerization. The molecular weight was monitored with time by gel permeation chromatography (GPC) to confirm the completion of polymerization of component A (EOVE).

Then the component B (MOVE) was added by 12 mmol to carry out a polymerization. After the completion of polymerization of the component B was confirmed by GPC monitoring, 30 mmol of $HO(CH_2)_5COOEt$ were added to terminate the polymerization reaction. The reaction mixture was diluted with dichloromethane, then washed three times with 0.6M hydrochloric acid and three times with distilled water. The obtained organic phase was concentrated and dried on an evaporator to obtain a block polymer of Poly[EOVE-b-MOVE]-$O(CH_2)_5COOEt$.

The synthesized compound was identified by GPC and NMR. In particular, the portion bonded at an end was identified by confirming the presence of the end portion in a spectrum of high molecular weight members by the DOSY NMR. $Mn=2.1\times10^4$ and $Mn/Mw=1.4$, wherein Mn is a number-average molecular weight and Mw is a weight-average molecular weight.

The end ester site of the obtained poly[EOVE-b-MOVE]-$O(CH_2)_5COOEt$ was hydrolyzed to obtain desired poly[EOVE-b-MOVE]-$O(CH_2)_5COOH$ which was identified by NMR.

26 parts by weight of the obtained block polymer having a carboxylic acid at the end were agitated with 200 parts by weight of an aqueous solution of sodium hydroxide of pH 11 at 0° C. for 3 days, to obtain a solution of sodium carboxylate polymer in which the polymer was completely dissolved. The polymer was extracted with methylene chloride and dried by distilling off the liquid medium whereby the polymer was isolated.

25 parts by weight of the polymer were dissolved in 80 parts by weight of methylene chloride, and 10 parts by weight of phthalocyanine blue (manufactured by Toyo Ink Co.) were added and dispersed. The dispersion was added dropwise to 800 parts by weight of distilled water with stirring, and 200 parts by weight of ethylene glycol were added. The mixture was left to stand in an open state for 3 hours at 40° C. and methylene chloride was completely distilled off to obtain an ink.

Evaluation Under a Cryogenic Transmission Electron Microscope

An appropriate amount of thus prepared ink solution was placed on a mesh using a squirt. In this example, a microgrid was employed as the mesh.

Then a filter paper was lightly pressed to absorb excess water so that the ink (water) was not excessive in the later cooling step.

This operation has to be conducted carefully. If the pressure is too strong, all the ink may be absorbed, or the microcapsules may be damaged.

Then the mesh was set on a rapid freezing apparatus (Leica CM-10). In this example, liquid nitrogen was used as the coolant, and liquid propane was used to cool the liquid nitrogen. In this manner the ink on the mesh was frozen rapidly.

It was placed on a cryotransfer (manufactured by Gatan) in this state and transferred to a holder for a transmission electron microscope. It is important to execute this operation while the sample is placed in liquid nitrogen. It is also necessary to pay attention not to damage the sample by bubbling of liquid nitrogen.

The holder bearing the sample was introduced into a cryogenic transmission electron microscope for observation. In this example, a transmission electron microscope TECNA 120 of EFI Japan was employed. Observation conditions are: acceleration voltage: 200 kV, energy filter width: 5 eV, and observation temperature: −180° C.

A zero loss image obtained in this observation is shown in FIG. 1, which shows a particle size of about 200 nm.

Comparative Example 1 (observation under an ordinary transmission electron microscope)

A polymer was synthesized in the same manner as in the synthesis of block polymer in Example 1.

A small amount of the aforementioned ink was dropped using a squirt on a collodion film on a mesh (200 mesh, manufactured by Oken Shoji Co.) for a transmission electron microscope.

Then an excessive liquid medium (water) was removed with a filter paper, and the sample was dried in the air for about a half day.

Figure 5:
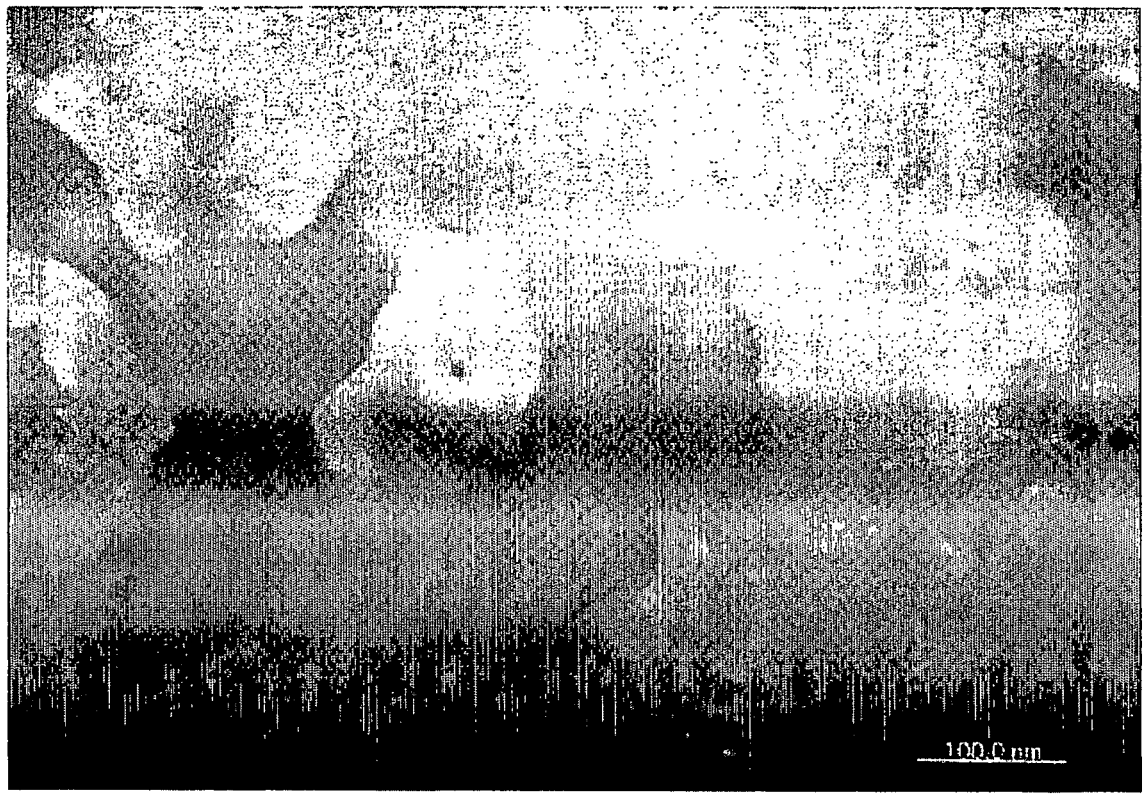
FIG. 5 is a photomicrograph (magnification: ×50,000) obtained with an ordinary transmission electron microscope in a comparative example of the present invention.

Then an observation was executed under a transmission electron microscope (H-800, manufactured by Hitachi Ltd.). This example is shown in FIG. 5. As shown therein, the microcapsules were destructed, so that the original shape in the ink was lost.

Example 2

Synthesis of Block Polymer

Synthesis was executed in the same manner as in Example 1.

Evaluation Under a Cryogenic Transmission Electron Microscope

An appropriate amount of the aforementioned ink was placed on a sample stage of cryogenic transfer for a scanning electron microscope.

Then the ink was cooled to −80° C. by a cryogenic transfer. In this state, it was introduced into a field emission scanning electron microscope (S-5000H, manufactured by Hitachi Ltd.), and was subjected to an observation at −100° C. under cooling with liquid nitrogen.

Comparative Example 2

Observation Under an Ordinary Scanning Electron Microscope

A polymer was synthesized in the same manner as in the synthesis of block polymer in Example 1, and an ink was prepared.

Then a well-washed Si substrate was adhered on a sample stage of a scanning electron microscope with a carbon tape.

A small amount of the aforementioned ink was taken by a squirt and dropped onto the surface of the Si substrate. Then it was left to stand in the air for several minutes.

By such standing, it is considered that water evaporates to a certain extent but still remains in a certain amount.

Then, in order to provide the sample with a conductivity, a thin film of Pt (50 Angstrom) was evaporated with an ion beam sputtering apparatus (VP-10 manufactured by Hitachi Ltd.).

Figure 6:
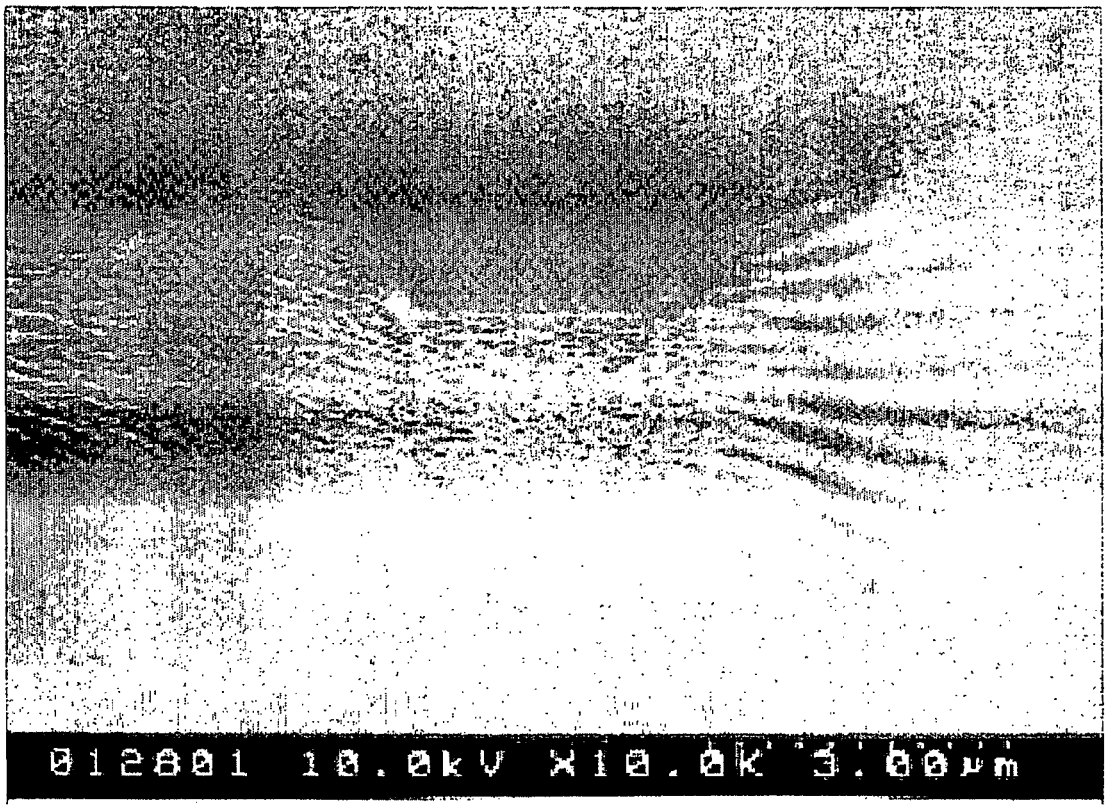
FIG. 6 is a photomicrograph (magnification: ×10,000) obtained with an ordinary transmission electron microscope in a comparative example of the present invention.

FIG. 6 shows a result of observation of this sample under a field emission scanning electron microscope (S-5000H, manufactured by Hitachi Ltd.). It was confirmed that the water was almost lost by placing in the chamber of the evaporation apparatus and in the sample chamber of the scanning electron microscope, whereby the shape of the microcapsules was destructed.

Also as the observation was carried out at a normal temperature, the membrane of such an organic sample melted because of the temperature elevation during electron beam irradiation for scanning electron microscopic observation.

Therefore, in the observation at the normal temperature with a scanning electron microscope, direct observation of the shape of the microcapsules was extremely difficult.

The invention claimed is:

1. An information acquiring method for acquiring information relating to a sample containing a pigment covered with a polymer in a liquid medium comprising the steps of:
   (a) preparing the sample;
   (b) rendering the liquid medium in the sample to an amorphous medium by rapid freezing so that the covering polymer is not disrupted; and
   (c) subjecting the sample with the amorphous medium to a microscopic observation under vacuum to acquire information relating to the sample.

2. The method according to claim 1, wherein the pigment is included in a microcapsule.

3. The method according to claim 1, wherein the information is at least one of morphology, quality and quantity of the pigment.

4. The method according to claim 1, wherein the step (c) comprises a step of irradiating the pigment in the amorphous medium with an electron beam, where the information is acquired by an electron energy loss spectroscopy.

5. The method according to claim 1, wherein the step (c) comprises a step of irradiating the pigment in the amorphous medium with an electron beam, wherein the information is acquired by an energy filtering electron microscopy.

* * * * *